(12) United States Patent
Zhan et al.

(10) Patent No.: US 11,357,945 B2
(45) Date of Patent: Jun. 14, 2022

(54) NASAL PAD FOR RESPIRATORY MASK AND RESPIRATORY MASK

(71) Applicant: BMC MEDICAL CO., LTD., Beijing (CN)

(72) Inventors: Yifeng Zhan, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 439 days.

(21) Appl. No.: 16/476,232

(22) PCT Filed: Dec. 14, 2017

(86) PCT No.: PCT/CN2017/116048
§ 371 (c)(1),
(2) Date: Jul. 5, 2019

(87) PCT Pub. No.: WO2018/126864
PCT Pub. Date: Jul. 12, 2018

(65) Prior Publication Data
US 2019/0351170 A1    Nov. 21, 2019

(30) Foreign Application Priority Data

Jan. 6, 2017   (CN) .......................... 201710010122.2

(51) Int. Cl.
*A61M 16/06* (2006.01)
*A61M 16/00* (2006.01)

(52) U.S. Cl.
CPC .... *A61M 16/0672* (2014.02); *A61M 16/0003* (2014.02); *A61M 16/0616* (2014.02); *A61M 16/0683* (2013.01); *A61M 2202/0208* (2013.01)

(58) Field of Classification Search
CPC .......... A61M 16/0672; A61M 16/0003; A61M 16/0616; A61M 16/0683; A61M 16/06;
(Continued)

(56) References Cited

U.S. PATENT DOCUMENTS 4,782,832 A   11/1988   Trimble et al.
6,431,172 B1   8/2002   Bordewick
(Continued)

FOREIGN PATENT DOCUMENTS

CN   203749967 U   8/2014
CN   103143097 A   8/2015
(Continued)

*Primary Examiner* — Samchuan C Yao
*Assistant Examiner* — Sarah B Lederer
(74) *Attorney, Agent, or Firm* — Volpe Koenig (57) ABSTRACT

A nasal pad for respiratory mask and a respiratory mask. The nasal pad comprises a nasal pad body and nasal plugs. Each nasal plug comprises a nasal plug body. The nasal plug bodies are fixedly connected to the nasal pad body. The nasal pad body comprises extend-retract adjustment sections. The extend-retract adjustment sections are provided with an extended length and a retracted length. The extend-retract adjustment sections are configured in a way that the length thereof can be adjusted between the extended length and the retracted length, thus varying the distance between the two nasal plug bodies. One purpose of the nasal pad is for use in the respiratory mask.

12 Claims, 5 Drawing Sheets

(58) Field of Classification Search
CPC .......... A61M 16/0605; A61M 16/0666; A61M 16/00; A62B 23/06
See application file for complete search history.

(56) References Cited

U.S. PATENT DOCUMENTS

| | | | | |
|---|---|---|---|---|
| 6,763,832 B1* | 7/2004 | Kirsch | ............... | A61M 16/0666 128/203.22 |
| 2005/0279351 A1 | 12/2005 | Lewis et al. | | |
| 2006/0107958 A1* | 5/2006 | Sleeper | ............... | A61M 16/0611 128/206.11 |
| 2011/0240035 A1* | 10/2011 | Gillies | ............... | A61M 16/0666 128/207.18 |
| 2014/0000626 A1* | 1/2014 | O'Connor | ......... | A61M 16/0875 128/207.18 |
| 2014/0166021 A9 | 6/2014 | Genger et al. | | |
| 2015/0013678 A1 | 1/2015 | McAuley et al. | | |
| 2015/0297855 A1 | 10/2015 | McAuley et al. | | |
| 2016/0015925 A1* | 1/2016 | Harrison | ........... | A61M 16/0605 128/201.13 |
| 2016/0074611 A1* | 3/2016 | Higgins | ............ | A61M 16/0605 128/206.24 |

FOREIGN PATENT DOCUMENTS

| | | | | |
|---|---|---|---|---|
| CN | 204637203 U | * | 9/2015 | |
| CN | 204637203 U | | 9/2015 | |
| CN | 204910378 U | | 12/2015 | |
| CN | 105283211 A | | 7/2017 | |
| DE | 102008010475 A1 | | 8/2009 | |
| WO | WO-2005097247 A1 | * | 10/2005 | ........ A61M 16/0066 |
| WO | 2009151344 A1 | | 12/2009 | |
| WO | WO2014207594 A1 | | 12/2014 | |
| WO | 2016157103 A1 | | 10/2016 | |

\* cited by examiner

NASAL PAD FOR RESPIRATORY MASK AND RESPIRATORY MASK

CROSS REFERENCE TO RELATED APPLICATIONS

The present application is a 35 USC § 371 national stage application of PCT/CN2017/116048, which was filed Dec. 14, 2018 and claims priority to Chinese Patent Application No. 201710010122.2, which was filed on Jan. 6, 2017, the entire content of both are incorporated herein by reference.

FIELD OF THE INVENTION

The present invention relates to the field of respiratory masks, particularly to a nasal pad for respiratory mask and a respiratory mask.

BACKGROUND OF THE INVENTION

Non-intrusive positive pressure ventilation is widely used in the treatment of respiratory problems such as obstructive sleep apnea (OSA), chronic obstructive pulmonary disease (COPD), upper airway resistance syndrome (UARS) and congestive heart failure, etc. Such a treatment approach utilizes a fan to provide continuous positive airway pressure (CPAP) or varying positive airway pressure to the patient through a tube line, instead of inserting a tube into the airway of the patient through a surgical operation.

The existing non-intrusive ventilation treatment process usually requires a respiratory mask. Respiratory masks may be categorized into nasal masks, oral-nasal masks, nasal pad masks and facial masks.

Wherein, the typical structure of a nasal pad mask comprises a frame, a nasal pad, a connection pipe, and a head band connecting arm. The nasal pad is fixed on the frame, and the nasal pad and the frame together form a gas chamber. The head band connecting arm is fixed on the frame, and is configured to connect a head band. The nasal pad is provided with nasal plugs and a nasal pad gas inlet. The nasal plugs may be inserted into the user's nostrils, and the nasal pad gas inlet corresponds to a frame gas inlet in the frame. The connection pipe is connected with the frame gas inlet to convey gas into the gas chamber, so that the gas enters into the user's body via the nasal plugs.

Existing nasal pad masks are usually provided with a plurality of nasal pads with nasal plugs spaced apart at different spacings to adapt to the nostril spacings of different users. In order to find out a nasal pad suitable for a user, the user has to try different nasal pads with nasal plug spaced apart at different spacings repeatedly. That process is cumbersome and inconvenient; in addition, a nasal pad mask equipped with a plurality of nasal pads with nasal plugs spaced apart at different spacings has higher cost.

Therefore, it is desirable to improve the existing nasal pads to solve at least one problem in the prior art.

SUMMARY OF THE INVENTION

The object of the invention is to provide a nasal pad for respiratory mask capable of adjusting the spacing between the nasal plugs and a respiratory mask including the nasal pad.

To attain the above object, according to a first aspect of the present invention, the present invention provides a nasal pad for respiratory mask, which comprises a nasal pad body and two nasal plugs, wherein the nasal pad body comprises a extend-retract adjustment section;

each of the nasal plugs comprises a nasal plug body fixedly connected to the nasal pad body;

the extend-retract adjustment section has extended length and retracted length;

the extend-retract adjustment section is configured in a way that the length thereof may be adjusted between the extended length and the retracted length, thus varying the distance between the two nasal plug bodies.

Preferably, the nasal pad body further comprises a fixed section that is configured in a way that the length thereof is not adjustable, and the nasal plug bodies are fixedly connected with the fixed section.

Preferably, the nasal pad body comprises at least two said extend-retract adjustment sections and at least two said fixed sections, wherein, the two nasal plug bodies are fixedly connected with different fixed sections;

two ends of at least one of the fixed sections fixedly connected with the nasal plug bodies are respectively provided with at least one of the extend-retract adjustment sections.

Preferably, the nasal plug body comprises a connecting portion and a nose contact portion that are connected sequentially, and the connecting portion is fixedly connected with the nasal pad body, wherein, the cross-sectional area of the connecting portion is the same as the cross-sectional area of the nose contact portion; or The maximum cross-sectional area of the connecting portion is smaller than the maximum cross-sectional area of the nose contact portion, and the nose contact portion is tapered gradually in a direction away from the connecting portion.

Preferably, the nasal plug further comprises at least one sealing rim, wherein, the sealing rim is fixedly connected with the outer surface of the nasal plug body;

the sealing rim extends in a direction opposite to the wearing direction of the nasal plugs.

Preferably, the extend-retract adjustment section employs corrugated tubes.

According to a second aspect of the present invention, the present invention provides a respiratory mask, which comprises a frame and the nasal pad for respiratory mask of the present invention, wherein, the frame comprises a frame gas inlet and a nasal pad fixing portion;

the nasal pad fixing portion is fitted with the nasal pad body so as to mount the nasal pad on the frame;

the frame gas inlet is configured to lead gas flow into the nasal pad.

Preferably, a first gas flow passage is arranged in the nasal pad body, and a nasal pad gas inlet is arranged in the side wall of the nasal plug body;

a second gas flow passage is arranged in the nasal plug body;

a third gas flow passage is arranged in the frame;

wherein, the nasal pad gas inlet communicates with the third gas flow passage;

the gas flow entering via the frame gas inlet flows through the third gas flow passage, the nasal pad gas inlet, the first gas flow passage, and the second gas flow passage sequentially.

Preferably, the nasal pad fixing portion comprises a nasal pad fixing portion body, and a communicating passage is arranged in the nasal pad fixing portion body;

the communicating passage is configured to communicate the first gas flow passage with the third gas flow passage;

Preferably, the nasal pad fixing portion further comprises a closing portion fixedly connected with the nasal pad fixing portion body;

the end of the first gas flow passage has an opening;

the closing portion is configured to fit with the opening so as to close the opening.

Preferably, the respiratory mask further comprises a length adjusting member;

the nasal pad comprises a fitting portion arranged on the nasal pad body;

the length adjusting member comprises a connecting portion and a sliding portion, wherein, the connecting portion is connected with the fitting portion;

the sliding portion is slidably fitted with the frame;

the length adjusting member may drive the fitting portion to slide along the frame, so that the length of the extend-retract adjustment section is adjusted between the extended length and the retracted length.

Preferably, a slide groove is provided on the frame, and the sliding portion comprises a slide block slidably fitted with the slide groove.

Preferably, a plurality of first positioning structures are provided on the frame;

a second positioning structure is provided on the length adjusting member;

the second positioning structure is fitted with one of the plurality of first positioning structures to fix the length adjusting member at a position on the frame.

A beneficial effect of the present invention is that the spacing between the nasal plugs can be adjusted easily by adjusting the length of the extend-retract adjustment section.

With the nasal pad for respiratory mask provided in the present invention, by adjusting the length of the extend-retract adjustment section between the extended length and the retracted length, the length of the extend-retract adjustment section may be selected according to the user's requirement, and thereby the spacing between the two nasal plug bodies may be adjusted according to the user's requirement.

Compared with the nasal pad masks in the prior art, which have to be equipped with a plurality of nasal pads with nasal plugs spaced apart at different spacings to adapt to the nostril spacings of different users, the distance between the two nasal plugs of the nasal pad in the present invention is adjustable. The user may wear a respirator mask assembled with the nasal pad in the present invention, and adjust the spacing between the nasal plugs to an appropriate state by adjusting the length of the extend-retract adjustment section. The user does not have to try nasal pads with nasal plugs at different spacings repeatedly; thus, the operation is simple and convenient. Furthermore, one nasal pad for respiratory mask provided in the present invention can meet the user's requirement. Compared with the existing respiratory masks that have to be equipped with a plurality of nasal pads, the nasal pad for respiratory mask provided in the present invention greatly reduces the cost of a respiratory mask.

Other features and advantages of the present invention will become clear through reading the following detailed description of the embodiments of the present invention with reference to the accompanying drawings.

BRIEF DESCRIPTION OF DRAWINGS

The accompanying drawings, which are incorporated in the specification and constitute a part of the specification, illustrate the embodiments of the present invention, and are used in conjunction with their description to explain the principles of the present invention.

In the figures.

1—nasal pad; 11—nasal pad body; 111—first gas flow passage; 1111—nasal pad gas inlet; 1112—opening; 112—first extend-retract adjustment section; 113—first fixed section; 114—second extend-retract adjustment section; 115—second fixed section; 116—third extend-retract adjustment section; 117—third fixed section; 118—fourth fixed section; 119—fitting portion; 12—nasal plug; 121—nasal plug body; 1221—second gas flow passage; 1222—connecting portion; 1223—nose contact portion; 12231—expanded portion; 12232—contracted portion; 122—sealing rim; 2—frame; 21—frame gas inlet; 22—third gas flow passage; 23—nasal pad fixing portion; 231—nasal pad fixing portion body; 2311—communicating passage; 232—closing portion; 24—slide groove; 25—first positioning structure; 3—length adjusting member; 31—connecting portion; 32—sliding portion; 321—slide block; 4—connection pipe; 5—head band connecting arm; 51—head band connecting portion.

DETAILED DESCRIPTION OF THE EMBODIMENTS

Hereunder some embodiments of the present invention will be detailed with reference to the accompanying drawings. It should be noted: unless otherwise specified, the relative arrangements, numerical expressions and values of the components and steps described in those embodiments don't constitute any limitation to the scope of the present invention.

In fact, the following description of at least one embodiment is only illustrative, and shall not be deemed as any limitation to the application or use of the present invention.

Techniques, methods and apparatuses known to those having ordinary skills in the art may not be discussed in detail, but, where appropriate, those techniques, methods and apparatuses shall be considered as a part of the specification.

In all examples shown and discussed here, any specific value shall be interpreted as being exemplary rather than limitative. Therefore, different values may be possible in other embodiments.

It should be noted that similar numbers and letters represent similar items in the following drawings. Therefore, once an item is defined in one of the drawings, it is not necessary to discuss it further in the follow-up drawings.

In order to solve the problem that it is inconvenient to adjust the spacing between the nasal plugs in the prior art, the present invention provides a nasal pad 1.

Figure 1:
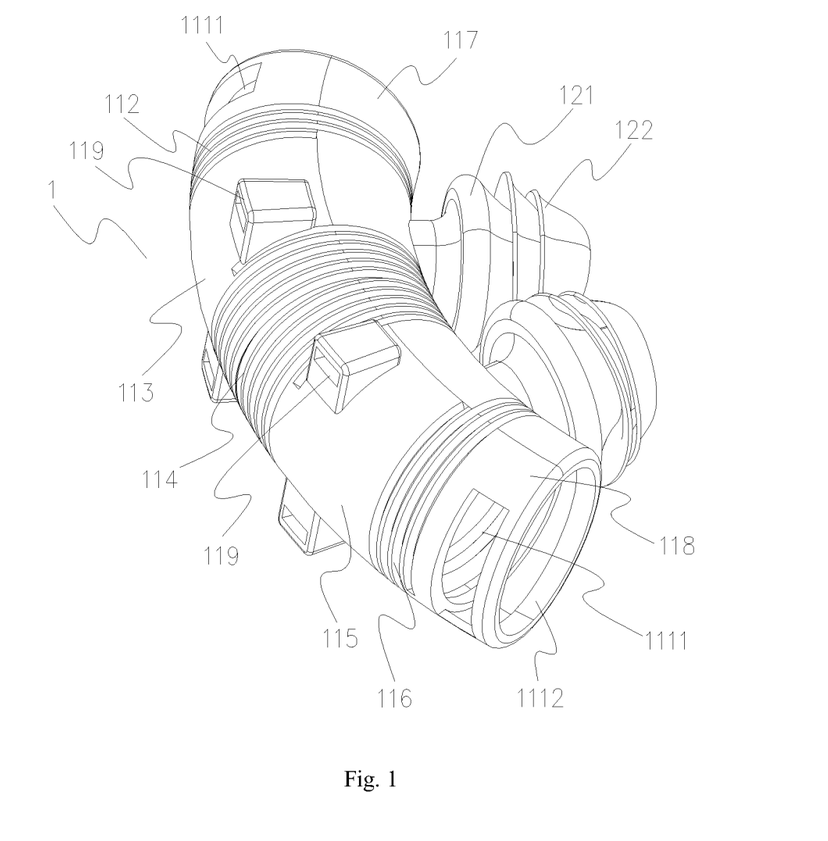
FIG. 1 is a schematic structural diagram of an embodiment of the nasal pad for respiratory mask in the present invention.
Figure 2:
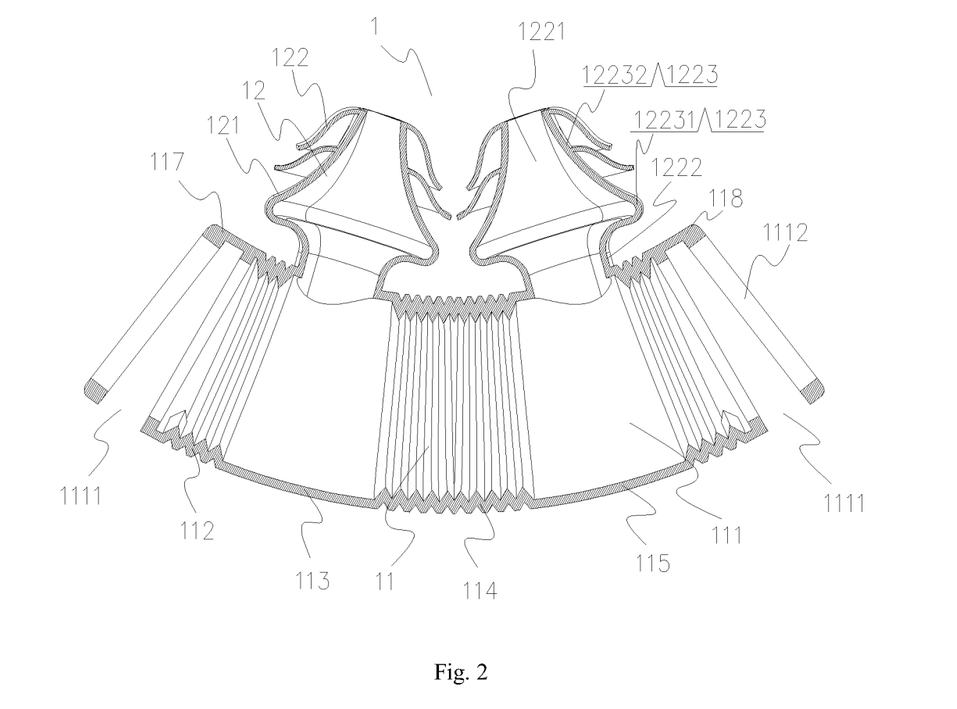
FIG. 2 is a sectional view of an embodiment of the nasal pad for respiratory mask in the present invention.
Figure 3:
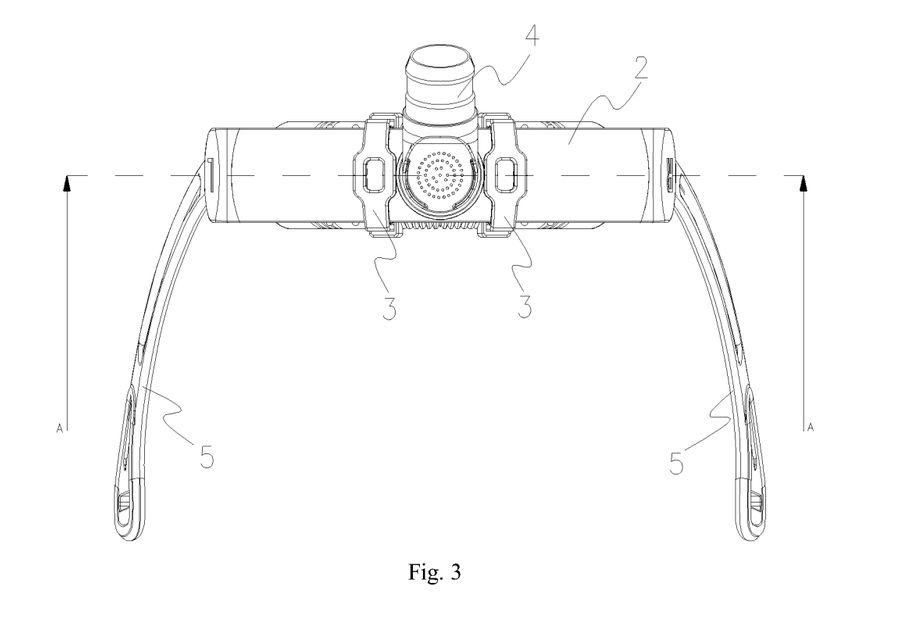
FIG. 3 is a schematic structural diagram of an embodiment of the respiratory mask in the present invention when viewed at a viewing angle.

As shown in FIGS. 1 and 2, the nasal pad 1 comprises a nasal pad body 11 and two nasal plugs 12. During use, the user may insert the two nasal plugs 12 into his/her nostrils respectively.

The shape of the nasal pad body 11 may be determined according to the actual requirement. For example, the nasal pad body 11 may be in a circular tube shape. Alternatively, the nasal pad body 11 may be in a rectangular tube shape.

The nasal plug 12 comprises a nasal plug body 121 fixedly connected with the nasal pad body 11. The fixed connection between the nasal plug body 121 and the nasal pad body 11 may be implemented by integral forming, plastic welding, or ultrasonic bonding, etc. Usually two nasal plugs 12 are provided, and accordingly two nasal plug bodies 121 are provided. The two nasal plug bodies 121 may be inserted into the two nostrils of the user respectively. The shape of the nasal plug body 121 may be determined according to the actual requirement. For example, in the length direction of the nasal plug body 121, the central portion of the nasal plug body 121 has an expanded area so that the nasal plug body 121 can be fitted in the nostril of the user more tightly.

The gas flow may flow into the nasal plug bodies 121 via the nasal pad body 11 and thereby enter into the body of the user. Alternatively, the gas flow may directly enter into the nasal plug bodies 121 through a tube line and thereby enter into the body of the user.

The nasal pad body 11 comprises a extend-retract adjustment section. The extend-retract adjustment section refer to portion of the nasal pad body 11 with a extend-retract length adjustment function. The length of the extend-retract adjustment section may be adjusted within a certain range.

The extend-retract adjustment section may be implemented in a variety of ways. For examples, the extend-retract adjustment section may employ corrugated tubes; or the extend-retract adjustment section may employ films; or the extend-retract adjustment section may employ bushing structures. All length-adjustable structures are applicable to the extend-retract adjustment section in the present invention.

The nasal pad body 11 may be composed of extend-retract adjustment section entirely. Alternatively, the nasal pad body 11 may have extend-retract adjustment section locally. The nasal plug bodies 121 may be fixedly connected with the extend-retract adjustment section, or the nasal plug bodies 121 may be fixedly connected with other sections of the nasal pad body 11 other than the extend-retract adjustment section.

The extend-retract adjustment section has extended length and retracted length. The extend-retract adjustment section is configured in a way that the length of it can be adjusted between the extended length and the retracted length, thus varying the distance between the two nasal plug bodies 121. The extended length refers to the length of the extend-retract adjustment section when the extend-retract adjustment section is extended as far as possible. The retracted length refers to the length of the extend-retract adjustment section when the extend-retract adjustment section is retracted as far as possible. The distance between the nasal plug bodies 121 refers to the distance between the geometrical centers of the two nasal plug bodies 121 at the joints between the nasal plug bodies 121 and the nasal pad body 11. The distance between the two nasal plug bodies 121 may also be referred to the spacing between the two nasal plug bodies 121. Usually, when the distance between the two nasal plug bodies 121 is close or equal to the distance between the geometrical centers of the two nostrils, the wearing comfortability of the nasal pad 1 is high. The distance between the two nasal plug bodies 121 may be changed by adjusting the length of the extend-retract adjustment section; thus, the adjustment is convenient and has low cost.

The user may adjust the length of the extend-retract adjustment section by applying force directly to the nasal pad body 11, so as to adjust the distance between the two nasal plug bodies 121.

With the nasal pad 1 provided in the present invention, by adjusting the length of the extend-retract adjustment section between the extended length and the retracted length, the length of the extend-retract adjustment section may be selected according to the user's requirement, and thereby the spacing between the two nasal plug bodies 121 may be adjusted according to the user's requirement.

Compared with the nasal pad masks in the prior art, which have to be equipped with a plurality of nasal pads with nasal plugs spaced apart at different spacings to adapt to the nostril spacings of different users, the distance between the two nasal plugs 12 of the nasal pad 1 in the present invention is adjustable. The user may wear a respirator mask assembled with the nasal pad 1 in the present invention, and adjust the spacing between the nasal plugs 12 to an appropriate state by adjusting the length of the extend-retract adjustment section. The user does not have to try nasal pads with nasal plugs at different spacings repeatedly; thus, the operation is simple and convenient. Furthermore, one nasal pad 1 provided in the present invention can meet different user requirements. Compared with the existing respiratory masks that have to be equipped with a plurality of nasal pads, the nasal pad 1 provided in the present invention effectively reduces the cost of a respiratory mask.

Preferably, the nasal pad body 11 further comprises a fixed section, which is configured in a way that the length thereof is not adjustable. Those skilled in the art should pay attention: in a case that the fixed section is made of an elastic material, the length of the fixed section may be changed slightly within the range of elastic deformation of the elastic material.

In the present invention, the nasal plug bodies 121 may be fixedly connected with the fixed section. The fixed connections between the nasal plug bodies 121 and the fixed section may be implemented by integral forming, plastic welding, or ultrasonic bonding, etc. Fixedly connecting the nasal plug bodies 121 with the fixed section rather than the extend-retract adjustment section is helpful for fixing the positions of the nasal plugs 12 on the nasal pad body 11 and avoiding any change of the spacing between the two nasal plug bodies 121 after the spacing is adjusted properly. Furthermore, by fixedly connecting the nasal plug bodies 121 with the fixed section in non-adjustable length, the structure of the extend-retract adjustment section is stable, and the length adjustment process of the extend-retract adjustment section is smoother.

According to an embodiment of the present invention, the nasal pad body 121 comprises at least two extend-retract adjustment sections and at least two fixed sections. The two nasal plug bodies 121 are fixedly connected with different fixed sections respectively. Wherein, two ends of at least one of the fixed sections fixedly connected with the nasal plug bodies 121 are respectively provided with at least one of the extend-retract adjustment sections. In that way, the distance from at least one nasal plug body 121 to the other nasal plug body 121 can be changed.

In the actual implementation, the quantity of the extend-retract adjustment sections and the quantity of the fixed sections may be set according to the actual requirement. For example, two extend-retract adjustment sections may be provided, and two fixed sections may be provided; here, the extend-retract adjustment sections and the fixed sections may be arranged in an alternating form. That is to say, a extend-retract adjustment section, a fixed section, another extend-retract adjustment section, and another fixed section may be arranged sequentially on the nasal pad body 11, and the two fixed sections are fixedly connected with one nasal plug body 121 respectively. The connections between the extend-retract adjustment sections and the fixed sections may be implemented by integral forming, gluing, or plastic welding, etc. Wherein, a extend-retract adjustment section is provided at each of the two ends of a fixed section that is fixedly connected with the nasal plug body 121; thus, the fixed section that is fixedly connected with the nasal plug body 121 can be moved with respect to the other fixed section, and thereby the distance between the two nasal plug bodies 121 can be changed.

In an embodiment of the nasal pad in the present invention, the nasal pad body 11 comprises a first extend-retract adjustment section 112, a first fixed section 113, a second extend-retract adjustment section 114, a second fixed section 115, and a third extend-retract adjustment section 116, which are connected sequentially. The two nasal plug bodies 121 are fixedly connected with the first fixed section 113 and the second fixed section 115 respectively. The connections between the extend-retract adjustment sections and the fixed sections may be implemented by integral forming, gluing, or plastic welding, etc.

Of course, those skilled in the art know that the structure of the nasal pad body 11 may not only have the above-mentioned sections. For example, as shown in FIG. 1, to increase the strength of the nasal pad body 11, a third fixed section 117 and a fourth fixed section 118 may be further provided at the free end of the first extend-retract adjustment section 112 and the free end of the third extend-retract adjustment section 116 respectively. That is to say, the nasal pad body 11 comprises a third fixed section 117, a first extend-retract adjustment section 112, a first fixed section 113, a second extend-retract adjustment section 114, a second fixed section 115, a third extend-retract adjustment section 116, and a fourth fixed section 118, which are connected sequentially.

Preferably, the extended length of the second extend-retract adjustment section 114 is greater than the extended length of the first extend-retract adjustment section 112 and the third extend-retract adjustment section 116, and the retracted length of the second extend-retract adjustment section 114 is greater than the retracted length of the first extend-retract adjustment section 112 and the third extend-retract adjustment section 116, so that the spacing between the two nasal plug bodies 121 can be adjusted more conveniently.

As shown in FIGS. 1 and 2, the two nasal plug bodies 121 are fixed to the fixed sections. Thus, in the adjustment process of the spacing between the two nasal plug bodies 121, the length of the first extend-retract adjustment section 112, the second extend-retract adjustment section 114, and the third extend-retract adjustment section 116 may be adjusted according to the requirement. The spacing between the two nasal plug bodies 121 will be changed as the length of the first extend-retract adjustment section 112, the second extend-retract adjustment section 114, and the third extend-retract adjustment section 116 is adjusted.

In another embodiment of the nasal pad in the present invention, the nasal plug body 121 comprises a connecting portion 1222 and a nose contact portion 1223 that are connected sequentially. The connecting portion 1222 is fixedly connected with the nasal pad body 11, and the fixed connection between them may be implemented by integral forming, plastic welding, or ultrasonic bonding, etc.

In the actual implementation, the cross-sectional area of the connecting portion 1222 may be the same as the cross-sectional area of the nose contact portion 1223.

Alternatively, the maximum cross-sectional area of the connecting portion 1222 may be smaller than the maximum cross-sectional area of the nose contact portion 1223, and the nose contact portion 1223 is tapered gradually in a direction away from the connecting portion 1222. Here, the nose contact portion 1223 may comprise two portions, i.e., an expanded portion 12231 and a contracted portion 12232 respectively. The expanded portion 12231 may be expanded outward in comparison with the connecting portion 1222 and the contracted portion 12232. That is to say, the expanded portion 12231 is expanded outward from the joints where the expanded portion 12231 is connected with the connecting portion 1222 and the contracted portion 12232. The above term "outward" refers to the direction away from the connecting portion 1222 and the contracted portion 12232. In use, the expanded portion 12231 may be fitted with the inner wall of a nostril of the user, and thereby the leak tightness can be improved when the nasal plug body 121 is used. The contracted portion 12232 is tapered gradually in the direction away from the connecting portion 1222.

Wherein, the connecting portion 1222, the expanded portion 12231, and the contracted portion 12232 may be connected together by integral forming, plastic welding, or ultrasonic bonding, etc.

In the above embodiment, the nasal plug bodies 121 can be worn comfortably, and attain a good sealing effect against the user's nostrils.

In another embodiment of the nasal pad in the present invention, the nasal plug 12 further comprises at least one sealing rim 122. The sealing rim 122 may be made of a soft and bacteriostatic material. For example, the sealing rim 122 may be made of silica gel. If a plurality of sealing rims 122 are provided, the nasal pad 1 can be fitted with the user's nostrils better, and thereby a better sealing effect can be attained.

The sealing rim 122 is fixedly connected with the outer surface of the nasal plug body 121. The fixed connection between the sealing rim 122 and the nasal plug body 121 may be implemented by integral forming, plastic welding, or ultrasonic bonding, etc.

The sealing rim 122 extends in a direction reversed from the wearing direction of the nasal plug 12. Here, the direction reversed from the wearing direction of the nasal plug 12 refers to a direction reversed from the direction in which the nasal plug 12 is inserted into a nostril of the user.

In the actual implementation process, the quantity of the sealing rims 122 may be set according to the actual requirement. For example, one sealing rim 122 may be provided; alternatively two sealing rims 122 may be provided, wherein, a first sealing rim 122 is fixedly connected with the end of the nasal plug body 121 away from the nasal pad body 11, and a second sealing rim 122 is closer to the nasal pad body 11 when compared with the first sealing rim 122. Optionally, the projection of the first sealing rim 122 on the second sealing rim 122 covers the second sealing rim 122 partially.

In yet another embodiment of the nasal pad in the present invention, the extend-retract adjustment sections are corrugated tubes. The extend-retract adjustment sections in a corrugated tube structure are advantageous for reducing the cost of the nasal pad 1 and improving the convenience of length adjustment of the extend-retract adjustment sections.

As shown in FIGS. 3-7, the present invention further provides a respiratory mask. The respiratory mask comprises a frame 2 and the nasal pad 1 according to the present invention.

The frame 2 comprises a frame gas inlet 21 and a nasal pad fixing portion 23.

The nasal pad fixing portion 23 is fitted with the nasal pad body 11 to mount the nasal pad 1 on the frame 2.

The fitting between the nasal pad fixing portion 23 and the nasal pad body 11 may be implemented in a variety of ways. For example, the nasal pad fixing portion 23 may be a protrusion on the frame 2, while the nasal pad body 11 is arranged with a hole or groove, so that the nasal pad 1 can be mounted to the frame 2 by means of the fitting between the protrusion and the hole or groove; alternatively, the nasal pad fixing portion 23 and the nasal pad body 11 may be fitted with each other by snap-fitting.

The frame gas inlet 21 is configured to lead gas flow into the nasal pad 1. In the actual implementation, the frame gas inlet 21 may communicate with the nasal pad body 11, which is to say, the nasal pad body 11 communicates with the frame gas inlet 21 via holes arranged in the nasal pad body 11. The holes arranged in the nasal pad body 11 may be in the extend-retract adjustment sections or fixed sections. In a case that the nasal pad body 11 is in a tubular shape, the holes via which the nasal pad body 11 communicates with the frame gas inlet 21 may be in the two ends of the nasal pad body 11. Preferably, the holes arranged in the nasal pad body 11 are in the fixed sections; alternatively, the frame gas inlet 21 directly communicates with the nasal plug body 121 through a tube line.

In an embodiment of the respiratory mask in the present invention, a first gas flow passage 111 is arranged in the nasal pad body 11, and a nasal pad gas inlet 1111 is arranged in the wall of the first gas flow passage 111. The nasal pad gas inlet 1111 may be arranged in a extend-retract adjustment section or fixed section as required. Preferably, the nasal pad gas inlet 1111 is arranged in a fixed section to avoid disturbance to the length adjustment function of the extend-retract adjustment sections.

A second gas flow passage 1221 is arranged in the nasal plug body 121. The second gas flow passage 1221 communicates with the first gas flow passage 111, so that the gas flow can flow through the nasal pad body 11 into the nasal plug body 121.

A third gas flow passage 22 is arranged in the frame 2. In a specific embodiment, the third gas flow passage 22 has a wall that is closed in the circumferential direction.

The nasal pad gas inlet 1111 communicates with the third gas flow passage 22, so that the gas flow can enter into the nasal pad gas inlet 1111 via the third gas flow passage 22. The quantity of the nasal pad gas inlets 1111 may be set according to the actual requirement. For example, one, two or more nasal pad gas inlets 1111 may be arranged.

The gas flow entering via the frame gas inlet 21 flows through the third gas flow passage 22, the nasal pad gas inlet 1111, the first gas flow passage 111, and the second gas flow passage 1221 sequentially, so that the gas flow is transferred into the user's body.

Furthermore, the nasal pad fixing portion 23 comprises a nasal pad fixing portion body 231. A communicating passage 2311 is arranged in the nasal pad fixing portion body 231. The quantity of the nasal pad fixing portions 23 usually corresponds to the quantity of the nasal pad gas inlets 1111. For example, if there are two nasal pad gas inlets 1111, two nasal pad fixing portions 23 are arranged.

The shape and structure of the nasal pad fixing portion body 231 may be determined according to the actual requirement. For example, the nasal pad fixing portion body 231 may be in a plate shape; alternatively, the nasal pad fixing portion body 231 may be a claw structure.

The nasal pad fixing portion body 231 is fitted with the nasal pad gas inlet 1111. The fitting between the nasal pad fixing portion body 231 and the nasal pad gas inlet 1111 may be implemented by inserting the nasal pad fixing portion body 231 into the nasal pad gas inlet 1111. Alternatively, the fitting between the nasal pad fixing portion body 231 and the nasal pad gas inlet 1111 may be implemented by snap fitting between the nasal pad fixing portion body 231 and the nasal pad gas inlet 1111.

The communicating passage 2311 is configured to enable the first gas flow passage 111 to communicate with the third gas flow passage 22. When the nasal pad fixing portion body 231 is fitted with the nasal pad gas inlet 1111, the communicating passage 2311 enables the first gas flow passage 111 to communicate with the third gas flow passage 22, so that the gas flow can enter into the first gas flow passage 111 from the third gas flow passage 22 via the communicating passage 2311.

Preferably, the nasal pad fixing portion 23 further comprises a closing portion 232. The closing portion 232 is fixedly connected with the nasal pad fixing portion body 231. The fixed connection between the nasal pad fixing portion body 231 and the closing portion 232 may be implemented by integral forming or welding, etc. The shape and structure of the closing portion 232 may be determined according to the actual requirement. For example, in the case that the nasal pad fixing portion body 231 is in a plate shape, the closing portion 232 may be in a block shape. Alternatively, in the case that the nasal pad fixing portion body 231 is a claw structure, the closing portion 232 may be a protrusion on the surface of the claw.

The ends of the first gas flow passage 111 have openings 1112. There is no particular restriction on the quantity of the openings 1112. Particularly, in the case that the nasal pad body 11 is in a tubular shape, both ends of the nasal pad body 11 may have an opening. That is to say, both ends of the first gas flow passage 111 have an opening 1112.

The closing portion 232 is configured to fit with the opening 1112 to close the opening 1112. The fitting between the closing portion 232 and the opening 1112 may be implemented by means of fitting between the closing portions 232 and the inner wall of the first gas flow passage 111. Optionally, the fitting between the closing portion 232 and the opening 1112 may be interference fit.

Figure 4:
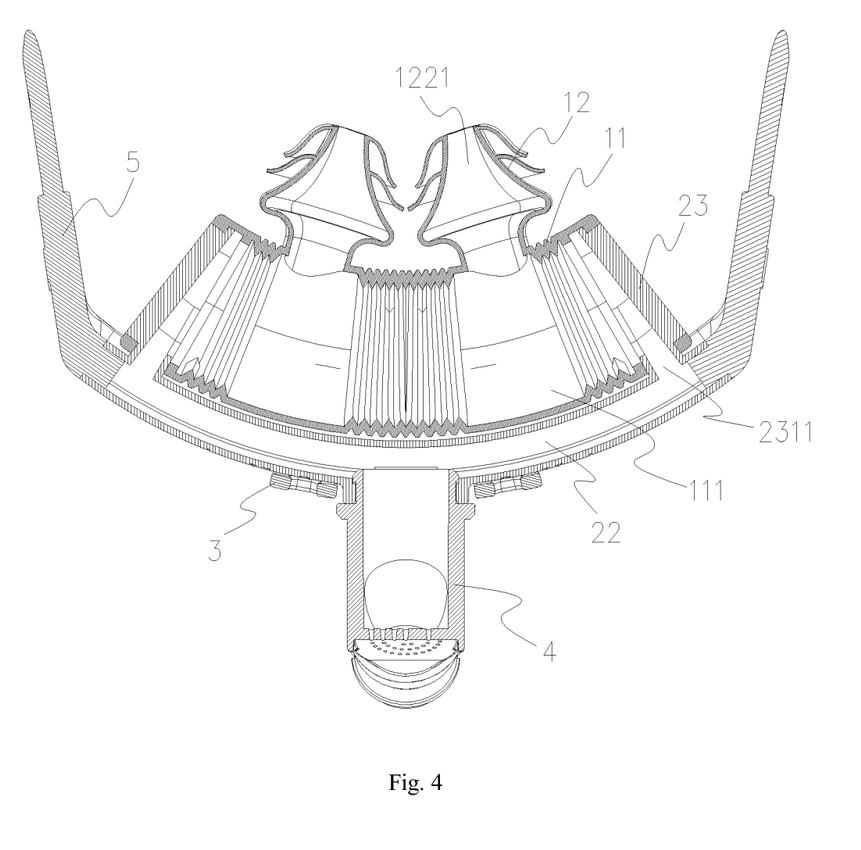
FIG. 4 is a sectional view A-A of the structure in FIG. 3.
Figure 5:
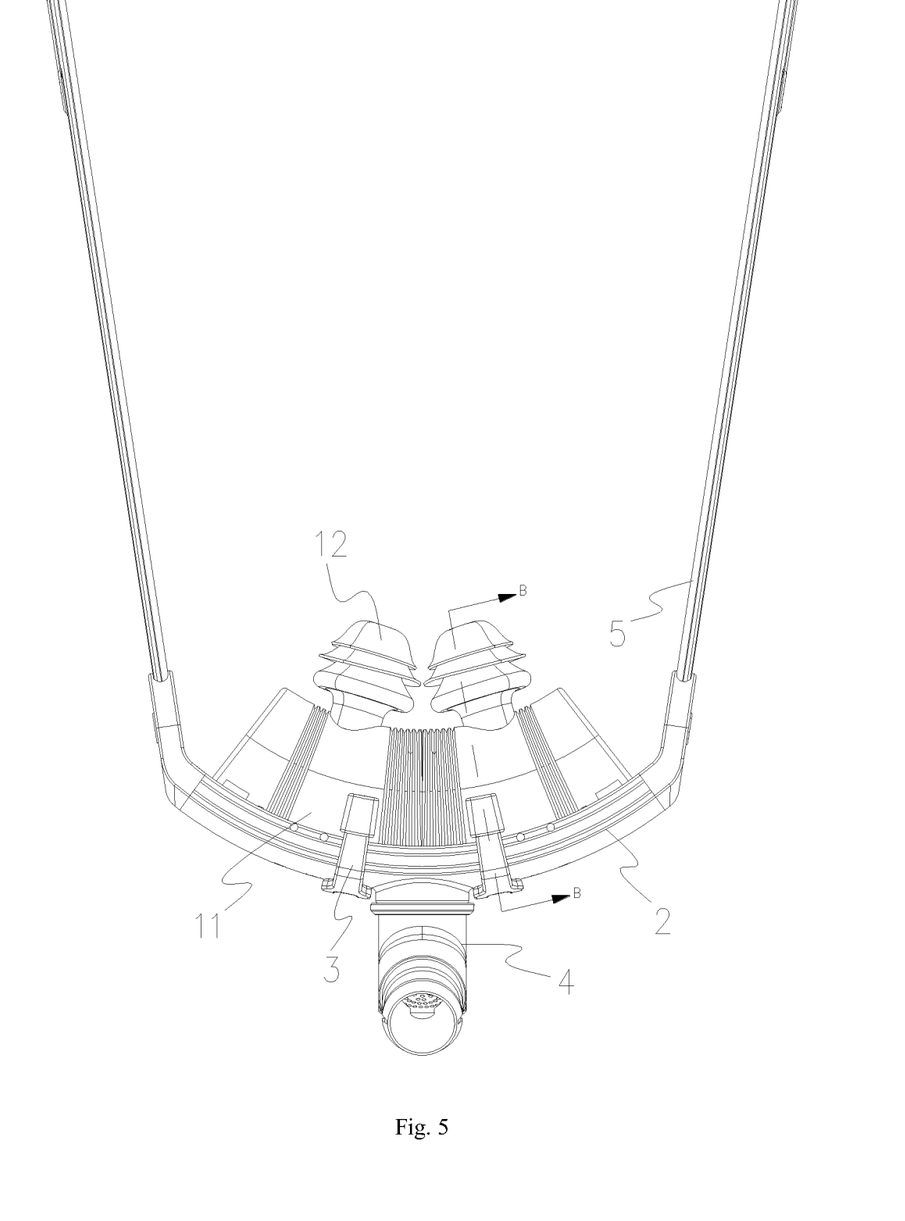
FIG. 5 is a schematic structural diagram of the respiratory mask in FIG. 3 when viewed at another viewing angle.
Figure 6:
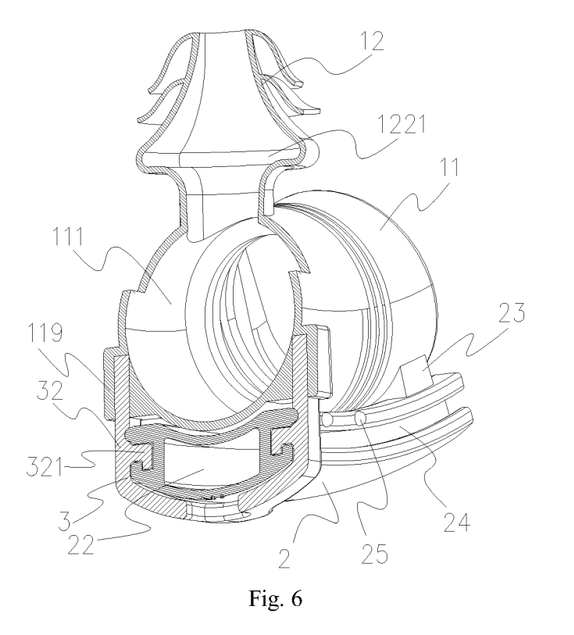
FIG. 6 is a sectional view B-B of the structure in FIG. 5.
Figure 7:
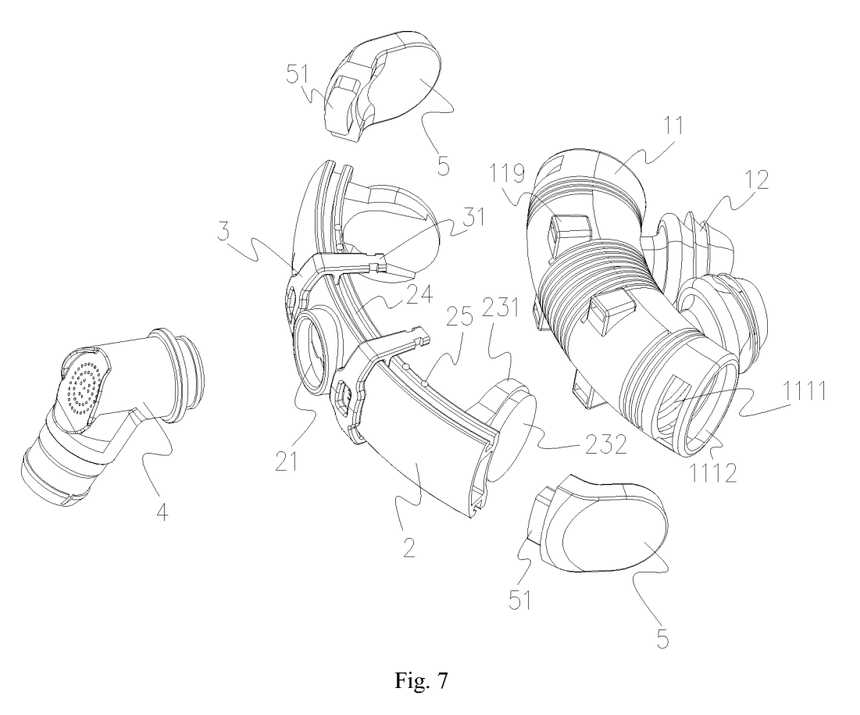
FIG. 7 is an exploded view of another embodiment of the respiratory mask in the present invention.

For example, in the embodiment of respiratory mask shown in FIG. 4, the nasal pad body 11 is in a tubular shape, and both ends of the tubular nasal pad body 11 have an opening 1112. Two nasal pad gas inlets 1111 are arranged in the wall of the first gas flow passage 111 in the nasal pad body 11. Two nasal pad fixing portions 23 are provided, and the nasal pad fixing portion body 231 and the closing portions 232 may be formed as an integral structure. The two nasal pad fixing portions 23 are inserted into the two nasal pad gas inlets 1111 respectively, and the nasal pad fixing portion body 231 is fitted with grooves in the inner wall of the first gas flow passage 111, so that the nasal pad fixing portion body 231 is positioned on the nasal pad body 11. The communicating passage 2311 enables the third gas flow passage 22 to communicate with the first gas flow passage 111. The closing portions 232 are fitted with the inner wall of the nasal pad body 11 to close the openings 1112 at the two ends of the tubular nasal pad body 11. The ends of the closing portions 232 are flush with the ends of the openings 1112 of the nasal pad body 11 respectively. When the respiratory mask is used, the gas flow entering via the frame gas inlet 21 flows through the third gas flow passage 22, the communicating passage 2311, the first gas flow passage 111, and the second gas flow passage 1221 sequentially, and thereby enters into the user's body.

In another embodiment of the respiratory mask in the present invention, the respiratory mask further comprises a length adjusting member 3. The length adjusting member 3 comprises a connecting portion 31 and a sliding portion 32.

The nasal pad body 11 comprises a fitting portion 119, the connecting portion 31 is connected with the fitting portion 119, so that the length adjusting member 3 and the nasal pad body 11 are connected together. The fitting portion 119 may be a boss arranged on the outer surface of the nasal pad body 11. The fitting portion 119 may be connected with the nasal pad body 11 by welding, gluing, or integral forming, etc.

The connection between the connecting portion 31 and the fitting portion 119 may be implemented in a variety of ways. For example, the connecting portion 31 may be connected with the fitting portion 119 by snap fitting; alternatively, the connecting portion 31 may be connected with the fitting portion 119 by gluing; alternatively, the connecting portion 31 may be connected with the fitting portion 119 by bolting.

The sliding portion 32 is slidably fitted with the frame 2. The length adjusting member 3 drives the fitting portion 119 to slide along the frame 2, so that the length of the extend-retract adjustment sections can be adjusted between the extended length and the retracted length. When the length adjusting member 3 slides along the frame 2, the fitting portion 119 connected with the connecting portion 31 of the length adjusting member 3 moves together with the length adjusting member 3 so that the length of the extend-retract adjustment sections is changed and thereby the distance between the two nasal plug bodies 121 is changed.

In the actual implementation, a slide groove 24 may be arranged on the frame 2, and the sliding portion 32 may comprise a slide block 321 slidably fitted with the slide groove 24. By means of the slide fitting between the slide block 321 and the slide groove 24, the length adjusting member 3 can slide with respect to the frame 2, and the purpose of adjusting the length of the extend-retract adjustment sections can be attained. Furthermore, the slide groove 24 may be a slide groove with openings at the ends, so that the sliding portion 32 of the length adjusting member 3 can be assembled into the slide groove 24 more conveniently.

The length adjusting member 3 preferably is an integrally formed structure. Alternatively, the connecting portion 31 and the sliding portion 32 may be fixed together by plastic welding or gluing.

Preferably, a plurality of first positioning structures 25 are provided on the frame 2. A second positioning structure (not shown in the figures) is provided on the length adjusting member 3.

The second positioning structure is fitted with one of the plurality of first positioning structures 25 to fix the length adjusting member 3 at a position on the frame 2.

The second positioning structure may be a protrusion or groove, and the first positioning structure 25 may be a groove or protrusion fitted with the second positioning structure.

When the length adjusting member 3 slides to such an extent that a first positioning structure 25 is fitted with the second positioning structure, the position of the length adjusting member 3 on the frame 2 can be fixed. When certain force is applied to the length adjusting member 3, the length adjusting member 3 can be adjusted so that the second positioning structure is fitted with a different first positioning structure 25.

The arrangement of the second positioning structure and the first positioning structures 25 is advantageous for keeping the length adjusting member 3 at a position on the frame 2 to prevent the distance between the two nasal plugs 12 from changed uncontrollably after the distance is adjusted to an appropriate value.

Furthermore, numbers, letters, or symbols corresponding to the first positioning structures 25 may be arranged on the frame 2, and a window for viewing the numbers, letters, or symbols may be arranged on the length adjusting member 3. When the length adjusting member 3 slides to such an extent that the second positioning structure is fitted with a first positioning structure 25, the user may view a corresponding number, letter, or symbol through the window on the length adjusting member 3, and thereby the position of the length adjusting member 3 on the frame 2 can be ascertained. In that way, the user can clearly know the position of the length adjusting member 3 on the frame 2.

In another embodiment of the respiratory mask in the present invention, the respiratory mask further comprises a connection pipe 4 and a head band connecting arm 5.

The connection pipe 4 is connected with the frame gas inlet 21 to convey the gas into the frame gas inlet 21. The connection between the connection pipe 4 and the frame gas inlet 21 may be implemented by means of snap-fit connection, magnetic connection, mechanical interlocking, or frictional connection, etc. Preferably, the connection between the connection pipe 4 and the frame gas inlet 21 is a ball-socket connection, so that the connection pipe 4 can rotate with respect to the frame 2. In use, the user may install or remove the connection pipe 4 as required.

The head band connecting arm 5 is connected with the frame 2, and a head band may be fixed to the head band connecting arm 5. The connection between the head band connecting arm 5 and the frame 2 may be implemented in a variety of ways. For example, the head band connecting arm 5 may be welded to the frame 2; alternatively, the head band connecting arm 5 may be connected to the frame 2 by snap fitting.

In an embodiment, the head band connecting arm 5 is provided with a head band connecting portion 51, the third gas flow passage 22 of the frame 2 has an opening, and the head band connecting arm 5 and the frame 2 are connected by means of the fitting between the head band connecting portion 51 and the opening. In that embodiment, the head band connecting portion 51 of the head band connecting arm 5 closes the opening of the third gas flow passage 22.

In a particular embodiment of the respiratory mask in the present invention, the nasal pad body 11 is in a tubular shape, a first gas flow passage 111 is arranged in the nasal pad body 11, and the two ends of the tubular nasal pad body 11 have an opening respectively. The nasal pad body 11 comprises a third fixed section 117, a first extend-retract adjustment section 112, a first fixed section 113, a second extend-retract adjustment section 114, a second fixed section 115, a third extend-retract adjustment section 116, and a fourth fixed section 118, which are arranged sequentially. The first fixed section 113 and the second fixed section 115 are provided with a fitting portion 119 respectively. The third fixed section 117 and the fourth fixed section 118 are provided with a nasal pad gas inlet 1111 respectively.

A second gas flow passage 1221 is arranged in the nasal plug 12. The nasal plug 12 comprises a nasal plug body 121 and a sealing rim 122. The nasal plug body 121 comprises a connecting portion 1222, an expanded portion 12231, and a contracted portion 12232, which are connected sequentially. The two nasal plug bodies 121 are fixedly connected with the first fixed section 113 and the second fixed section 115 respectively. Each nasal plug body 121 has two sealing rims 122.

A third gas flow passage 22 is arranged in the frame 2. The frame 2 comprises a frame gas inlet 21, nasal pad fixing portions 23, a slide groove 24, and first positioning structures 25. Wherein, two nasal pad fixing portions 23 are arranged. The nasal pad fixing portion 23 comprises a nasal pad fixing portion body 231 and a closing portion 232. A communicating passage 2311 is arranged in the nasal pad fixing portion body 231. The two nasal pad fixing portions 23 are inserted into the two nasal pad gas inlets 1111 respectively. The communicating passage 2311 enables the third gas flow passage 22 to communicate with the first gas flow passage 111. The two closing portions 232 are fitted with the first gas flow passage 111 respectively so as to close the openings 1112 at the two ends of the tubular nasal pad body 11.

The length adjusting member 3 comprises connecting portions 31, sliding portions 32, and a second positioning structure. Two length adjusting members 3 are arranged. The two connecting portions 31 are connected with the two fitting portions 119 respectively, and the slide blocks 321 of the two sliding portions 32 are slidably fitted with the slide groove 24. The length adjusting member 3 can slide along the slide groove 24 with respect to the frame 2, and the second positioning structure can be fitted with a first positioning structure 25.

The connection pipe 4 is rotatably connected with the frame gas inlet 21. The head band connecting portions 51 of the two head band connecting arms 5 are fitted with the openings at the two ends of the third gas flow passage 22 respectively to close the openings at the two ends of the third gas flow passage 22.

During use, the user applies certain force to the length adjusting member 3, so that the length adjusting member 3 slides along the slide groove 24 of the frame 2. As the length adjusting member 3 moves, the length of the first extend-retract adjustment section 112, the second extend-retract adjustment section 114, and the third extend-retract adjustment section 116 is changed. The distance between the two nasal plug bodies 121 on the first fixed section 113 and the second fixed section 115 is changed, and thereby the purpose of adjusting the spacing between the nasal plugs is attained.

When the length adjusting member 3 slides to such an extent that a first positioning structure 25 is fitted with the second positioning structure, the position of the length adjusting member 3 on the frame 2 can be fixed. When force in a different magnitude is applied to the length adjusting member 3, the length adjusting member 3 can be adjusted so that the second positioning structure is fitted with a different first positioning structure 25. The user may view the numbers on the frame 2 through the window on the length adjusting member 3, and thereby ascertain the position of the length adjusting member 3 on the frame 2 at this point.

The gas flow entering into the frame gas inlet 21 through the connection pipe 4 flows through the third gas flow passage 22, the communicating passage 2311, the first gas flow passage 111, and the second gas flow passage 1221 sequentially, and then enters into the user's body.

Although some embodiments of the present invention have been described in detail above in examples, those skilled in the art should appreciate that the above examples are provided only for the purpose of description rather than limiting the scope of the present invention. Those skilled in the art should appreciate that various modifications can be made to the above embodiments without departing from the scope and spirit of the present invention. The scope of the present invention is only defined by the appended claims.

The invention claimed is:

1. A respiratory mask comprising a frame and a nasal pad for respiratory mask, the frame comprises a frame gas inlet and a nasal pad fixing portion; the nasal pad for respiratory mask comprising a nasal pad body and two nasal plugs, wherein, each of the nasal plugs comprises a nasal plug body fixedly connected to the nasal pad body; the nasal pad body comprises extend-retract adjustment section(s); the extend-retract adjustment section has extended length and retracted length; the extend-retract adjustment section is configured in a way that the length thereof may be adjusted between the extended length and the retracted length, thus varying the distance between the two nasal plug bodies; the nasal pad fixing portion is fitted with the nasal pad body so as to mount the nasal pad on the frame; wherein the nasal pad fixing portion further comprises a nasal pad fixing portion body, and the nasal pad fixing portion is fitted with the nasal pad body by inserting the nasal pad fixing portion body into a nasal pad gas inlet arranged in the peripheral wall of the nasal pad body; the frame gas inlet is configured to lead gas flow into the nasal pad.

2. The respiratory mask of claim 1, wherein, a first gas flow passage is arranged in the nasal pad body; a second gas flow passage is arranged in the nasal plug body; a third gas flow passage is arranged in the frame; wherein, the nasal pad gas inlet communicates with the third gas flow passage; the gas flow entering via the frame gas inlet flows through the third gas flow passage, the nasal pad gas inlet, the first gas flow passage, and the second gas flow passage sequentially.

3. The respiratory mask of claim 2, wherein, a communicating passage is arranged in the nasal pad fixing portion body; the communicating passage is configured to communicate the first gas flow passage with the third gas flow passage.

4. The respiratory mask of claim 3, wherein the nasal pad fixing portion further comprises a closing portion fixedly connected with the nasal pad fixing portion body;
   the end of the first gas flow passage has an opening;
   the closing portion is configured to fit with the opening so as to close the opening.

5. The respiratory mask of claim 1, wherein
   the respiratory mask further comprises a length adjusting member;
   the nasal pad comprises a fitting portion arranged on the nasal pad body;
   the length adjusting member comprises a connecting portion and a sliding portion, wherein,
   the connecting portion is connected with the fitting portion;
   the sliding portion is slidably fitted with the frame;
   the length adjusting member may drive the fitting portion to slide along the frame, so that the length of the extend-retract adjustment section is adjusted between the extended length and the retracted length.

6. The respiratory mask of claim 5, wherein a slide groove is provided on the frame, and the sliding portion comprises a slide block slidably fitted with the slide groove.

7. The respiratory mask of claim 6, wherein
a plurality of first positioning structures are provided on the frame;
a second positioning structure is provided on the length adjusting member;
the second positioning structure is fitted with one of the plurality of first positioning structures to fix the length adjusting member at a position on the frame.

8. The respiratory mask of claim 1, wherein the nasal pad body further comprises a fixed section that is configured in a way that the length thereof is not adjustable, and the nasal plug bodies are fixedly connected with the fixed section.

9. The respiratory mask of claim 8, wherein the nasal pad body comprises at least two said extend-retract adjustment sections and at least two said fixed sections, wherein,
the two nasal plug bodies are fixedly connected with different fixed sections;
two ends of at least one of the fixed sections fixedly connected with the nasal plug bodies are respectively provided with at least one of the extend-retract adjustment sections.

10. The respiratory mask of claim 1, wherein the nasal plug body comprises a connecting portion and a nose contact portion that are connected sequentially, and the connecting portion is fixedly connected with the nasal pad body, wherein,
the cross-sectional area of the connecting portion is the same as the cross-sectional area of the nose contact portion; or
the maximum cross-sectional area of the connecting portion is smaller than the maximum cross-sectional area of the nose contact portion, and the nose contact portion is tapered gradually in a direction away from the connecting portion.

11. The respiratory mask of claim 1, wherein the nasal plug further comprises at least one sealing rim, wherein,
the sealing rim is fixedly connected with the outer surface of the nasal plug body;
the sealing rim extends in a direction opposite to the wearing direction of the nasal plugs.

12. The respiratory mask of claim 1, wherein the extend-retract adjustment section employs corrugated tubes.

* * * * *